(12) United States Patent
Fedele

(10) Patent No.: US 11,291,385 B2
(45) Date of Patent: Apr. 5, 2022

(54) SYSTEM FOR CONTROLLING ASSISTIVE TECHNOLOGIES AND RELATED METHOD

(71) Applicant: LIQUIDWEB S.r.l., Siena (IT)

(72) Inventor: Pasquale Fedele, Siena (IT)

(73) Assignee: LIQUIDWEB S.r.l., Siena (IT)

( * ) Notice: Subject to any disclaimer, the term of this patent is extended or adjusted under 35 U.S.C. 154(b) by 0 days.

(21) Appl. No.: 15/760,972

(22) PCT Filed: Sep. 13, 2016

(86) PCT No.: PCT/IB2016/055442
§ 371 (c)(1),
(2) Date: Mar. 16, 2018

(87) PCT Pub. No.: WO2017/046698
PCT Pub. Date: Mar. 23, 2017

(65) Prior Publication Data
US 2019/0104968 A1    Apr. 11, 2019

(30) Foreign Application Priority Data
Sep. 16, 2015   (IT) .................. 102015000052009

(51) Int. Cl.
*A61B 5/11* (2006.01)
*G06F 3/01* (2006.01)
(Continued)

(52) U.S. Cl.
CPC .............. *A61B 5/11* (2013.01); *A61B 5/1103* (2013.01); *A61B 5/369* (2021.01); *A61B 5/377* (2021.01);
(Continued)

(58) Field of Classification Search
None
See application file for complete search history.

(56) References Cited

U.S. PATENT DOCUMENTS

| | | | |
|---|---|---|---|
| 5,967,996 A | 10/1999 | Kadota et al. | |
| 8,217,900 B1 * | 7/2012 | Bowen ................. | A61F 4/00 345/168 |

(Continued)

FOREIGN PATENT DOCUMENTS

| | | |
|---|---|---|
| CN | 101201696 A | 6/2008 |
| CN | 101391129 A | 3/2009 |

(Continued)

OTHER PUBLICATIONS

International Search Report and Written Opinion of the International Searching Authority for corresponding International Patent Application No. PCT/IB2016/055442 dated Feb. 1, 2017, 20 pages.
(Continued)

*Primary Examiner* — Curtis J King
(74) *Attorney, Agent, or Firm* — Merchant & Gould P.C.

(57) ABSTRACT

A system controls assistive technologies with an assistive tool for users with movement and/or communication disorders. The system includes an electronic communication interface, a biometric sensor, a calibration module and a processing unit. The interface presents users with stimuli associated with commands and/or information that the user might select. The sensor detects the user's biometric activity and generates a biometric electrical signal. During initial calibration, the calibration module records signal characteristics associated with a biometric electrical signal detected with voluntary biometric activity. The processing unit recognizes, based on the biometric electrical signal and the signal characteristics, the user's voluntary biometric activity and commands and/or information the user wants to select. The processing unit provides control signals to the interface and the assistive tool, based on the user's selection preferences. The interface presents stimuli based on the presentation control signal, if present, or presents a scan of stimuli.

17 Claims, 5 Drawing Sheets

(51) Int. Cl.
*G06F 3/0482* (2013.01)
*G06F 3/023* (2006.01)
*A61G 5/10* (2006.01)
*A61B 5/369* (2021.01)
*A61B 5/377* (2021.01)
*A61B 5/389* (2021.01)
*A61B 5/00* (2006.01)

(52) U.S. Cl.
CPC ............ *A61B 5/389* (2021.01); *A61B 5/7225* (2013.01); *A61G 5/10* (2013.01); *A61G 5/1051* (2016.11); *G06F 3/013* (2013.01); *G06F 3/015* (2013.01); *G06F 3/017* (2013.01); *G06F 3/0236* (2013.01); *G06F 3/0482* (2013.01); *A61G 2203/18* (2013.01); *A61G 2203/20* (2013.01)

(56) References Cited

U.S. PATENT DOCUMENTS

| | | | |
|---|---|---|---|
| 8,915,871 B2* | 12/2014 | Einav | A61B 5/1116 601/5 |
| 9,389,685 B1* | 7/2016 | Pathirage | G06F 3/015 |
| 2002/0171680 A1 | 11/2002 | Beranek et al. | |
| 2003/0171689 A1* | 9/2003 | Millan | A61B 5/0476 600/544 |
| 2004/0006422 A1 | 1/2004 | Fehr et al. | |
| 2004/0267320 A1* | 12/2004 | Taylor | A61F 2/72 607/2 |
| 2006/0074822 A1* | 4/2006 | Eda | G06F 3/015 706/14 |
| 2006/0125659 A1 | 6/2006 | Kim et al. | |
| 2006/0161218 A1* | 7/2006 | Danilov | A61B 5/0492 607/45 |
| 2006/0167530 A1* | 7/2006 | Flaherty | A61B 5/04001 607/62 |
| 2006/0241356 A1* | 10/2006 | Flaherty | A61B 5/04 600/301 |
| 2008/0294033 A1* | 11/2008 | Yamazaki | A61B 5/0478 600/407 |
| 2009/0005700 A1* | 1/2009 | Joshi | A61B 5/0488 600/546 |
| 2010/0160808 A1* | 6/2010 | Adachi | G06F 3/015 600/546 |
| 2010/0172733 A1* | 7/2010 | Chalubert | A61F 4/00 414/730 |
| 2011/0071416 A1 | 3/2011 | Terada et al. | |
| 2011/0238685 A1* | 9/2011 | Molina | A61B 5/0476 707/769 |
| 2011/0245708 A1* | 10/2011 | Finkel | A61B 5/0484 600/544 |
| 2012/0035765 A1* | 2/2012 | Sato | A61B 5/0476 700/264 |
| 2012/0101402 A1* | 4/2012 | Nguyen | A61B 5/7264 600/544 |
| 2012/0149467 A1* | 6/2012 | Heck | A63F 13/235 463/36 |
| 2012/0185096 A1 | 7/2012 | Rosenstein et al. | |
| 2012/0282578 A1* | 11/2012 | Chapman | G09B 5/06 434/178 |
| 2012/0289757 A1* | 11/2012 | Boyden | A61N 5/025 600/1 |
| 2012/0290051 A1* | 11/2012 | Boyden | A61N 1/0534 607/113 |
| 2013/0035734 A1* | 2/2013 | Fernandez | A61N 1/36021 607/3 |
| 2013/0060125 A1* | 3/2013 | Zeman | A61B 5/048 600/409 |
| 2013/0096453 A1* | 4/2013 | Chung | G06F 3/04847 600/544 |
| 2013/0100010 A1* | 4/2013 | Lee | G06F 3/015 345/156 |
| 2013/0127708 A1* | 5/2013 | Jung | A61B 5/0006 345/156 |
| 2013/0158445 A1* | 6/2013 | Kazerooni | A61H 3/00 601/35 |
| 2013/0158883 A1* | 6/2013 | Hasegawa | A61B 5/0476 702/19 |
| 2014/0058528 A1* | 2/2014 | Contreras-Vidal | A61B 5/04842 623/25 |
| 2015/0095228 A1* | 4/2015 | Su | G06Q 20/12 705/44 |
| 2016/0199203 A1* | 7/2016 | Adachi | A61B 5/0478 623/25 |
| 2017/0042713 A1* | 2/2017 | Nurmikko | A61B 5/0006 |
| 2017/0188933 A1* | 7/2017 | Huggins | A61B 5/4088 |
| 2017/0202518 A1* | 7/2017 | Furman | G06F 3/015 |
| 2018/0199840 A1* | 7/2018 | Loureiro | A61B 5/7267 |
| 2018/0261127 A1* | 9/2018 | Deffieux | A61B 8/00 |
| 2020/0187841 A1* | 6/2020 | Ayyad | G06N 3/0454 |
| 2020/0192478 A1* | 6/2020 | Alcaide | A61B 3/113 |

FOREIGN PATENT DOCUMENTS

| | | |
|---|---|---|
| EP | 2 613 222 A1 | 7/2013 |
| GB | 2 332 293 A | 6/1999 |
| JP | 2899194 B2 | 6/1999 |
| JP | 2003-248541 A | 9/2003 |
| JP | 2005-100366 A | 4/2005 |
| JP | 3116351 U | 12/2005 |
| JP | 2007-097946 A | 4/2007 |
| JP | 2012-053656 A | 3/2012 |
| KR | 10-2011-0136265 A | 12/2011 |
| WO | 2010/082496 A1 | 7/2010 |

OTHER PUBLICATIONS

Braincontrol: "BrainControl: The Frontier of Health 2.0", YouTube, 1 page (2015), retrieved from the Internet URL:https://www.youtube.com/watch?v=RLet3AMkuZ8.

Fedele, P. et al., "Braincontrol Basic Communicator: A Brain-Computer Interface Based Communicator for People with Severe Disabilities", Correct System Design, Springer International Publishing, pp. 487-494 (2014).

Yanco, H et al., "Wheelesley: A robotic wheelchair system: Indoor navigation and user interface", Assistive Technology and Artificial Intelligence, Springer-Verlag, 1458: 256-268 (1998).

Search Report for Chinese Patent application No. 2016800667169 dated Sep. 18, 2020, 3 pages.

Office Action for Japanese Patent Application No. 2018-514885 dated Mar. 15, 2021, 11 pages.

Decision to Grant for Japanese Patent Application No. 2018-514885 dated Aug. 26, 2021, 6 pages.

Standard operations of manual of Urbano V02, KDDI, p. 33 (2015), Internet: http://media.kiddi.com/app/publish/torisetsu/pdf/urbano_v02_torisetsu_shousai.pdf; Machine translation.

Honda, Y., "The Future Trend of Public and Private Use of Robotics", Journal of the Robotics Society of Japan, 30(10): 65-67 (2012); Machine translation.

Masuda, "One Step Communication", ASCII, 14(8): 422-423 (1990); Machine translation.

Kanoh, S., "A Basic Study on Brain-Computer Interface to Detect Foot Movement Imagery from EEG". IEICE Technical Report, 106(370): 9-12 (2006); Abstract.

* cited by examiner

SYSTEM FOR CONTROLLING ASSISTIVE TECHNOLOGIES AND RELATED METHOD

This application is a National Stage Application of PCT/IB2016/055442, filed 13 Sep. 2016, which claims benefit of Ser. No. 102015000052009, filed 16 Sep. 2015 in Italy and which applications are incorporated herein by reference. To the extent appropriate, a claim of priority is made to each of the above-disclosed applications.

TECHNICAL BACKGROUND OF THE INVENTION

Field of Application

The present invention in general relates to the technical field of assistive technologies and of man-machine interaction.

Indeed, the invention relates to a system for controlling assistive technologies, for users suffering from movement and/or communication disorders, and to a related method for controlling assistive technologies.

In particular, but not in a limiting way, the invention relates to a system of the Brain-Computer-Interface (BCI) type.

Description of the Known Art

As is known, there are millions of patients in the world with tetraplegia caused by pathologies such as Amyotrophic Lateral Sclerosis (ALS), spinal injuries, cerebral ischaemia etc. In many cases, such pathologies cause problems associated with communication, in addition to being associated with movement, thus resulting in significant changes in the lifestyle of such patients.

In the context of support and assistance to these disabled patients, the main assistive technologies that are commonly used belong to the following types: "Voice Control Systems", that is systems based on voice recognition; "Eye Tracking", that is systems for tracking pupil movements; other mechanical devices of various type.

Often, such devices can only be used a little or not at all by many patients for various reasons, first and foremost the difficulty for the patient to provide commands and/or pieces of information in a simple manner, for the patient, and in a reliable manner, that is exactly corresponding to the patient's will.

Amongst emerging technologies, "Brain Computer Interface" (BCI) technologies—that is a "brain-computer" type interface based on the interpretation of cerebral signals— have shown significant progress over the last few years, promoted by the increased comprehension of cerebral functions, by the evolution of electronic calculators and of sensoristics. However, these "BCI" technologies too have proved in many cases to be affected by the above-mentioned problems.

Overall, it may be affirmed that sufficiently usable and robust solutions, for a wide use to support persons with motion and communication disabilities, are lacking to date.

In light of the above, the need is strongly felt to provide systems and methods for controlling assistive technologies which can be used in a simple and reliable manner by users with motion and communication disabilities, and which at least partly overcome the drawbacks indicated above.

SUMMARY OF THE INVENTION

It is the object of the present invention to provide a system for controlling assistive technologies, which allows at least partly obviating the drawbacks indicated above with reference to the known art, and allows meeting the above-mentioned needs particularly felt in the technical field considered.

A method for controlling assistive technologies is also the object of the present invention.

BRIEF DESCRIPTION OF THE DRAWINGS

Further features and advantages of such a system according to the invention will become apparent from the following description of preferred embodiments thereof, given only by way of non-limiting, indicative example, with reference to the accompanying drawings, in which.

It is worth noting that equal or similar elements in the aforesaid drawings are indicated with the same numbers and/or letters.

DETAILED DESCRIPTION

Figure 1:
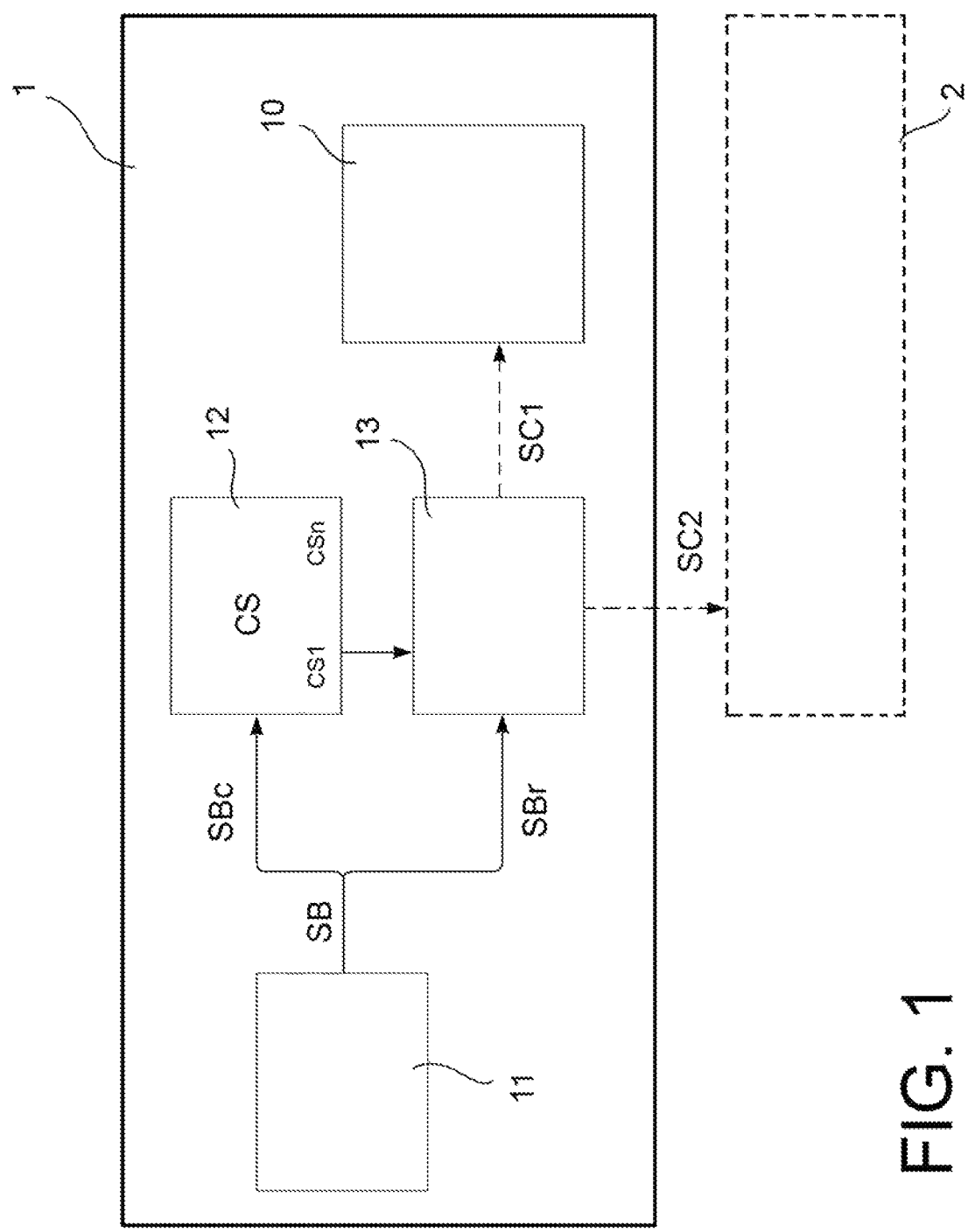
FIG. 1 shows a simplified functional diagram of a control system according to one embodiment of the present invention.
Figure 2:
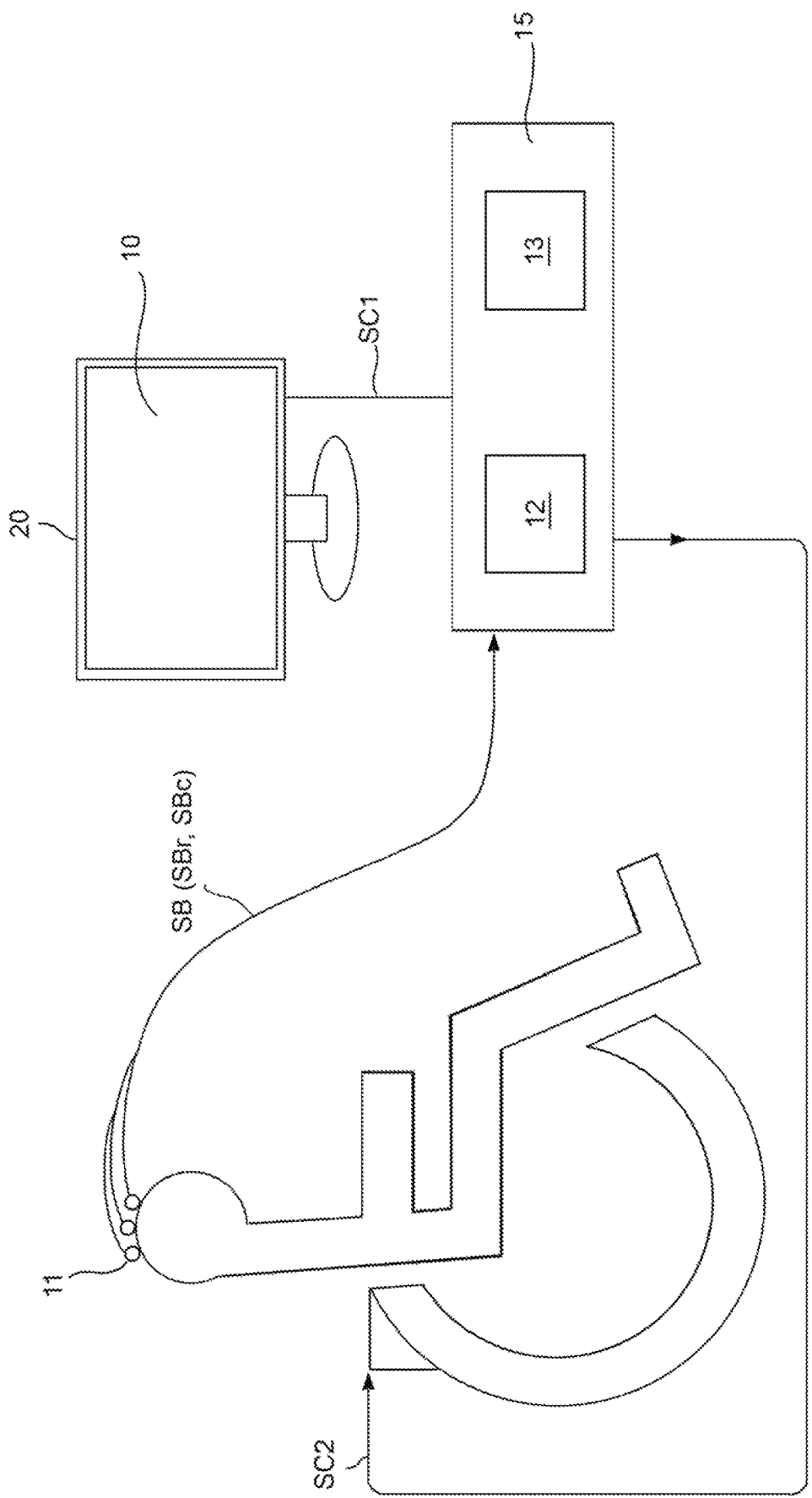
FIG. 2 shows an example of the use of components of the control system, within the context of assisting a user in a wheelchair.

With reference to FIGS. 1 and 2, a system 1 is now described for controlling assistive technologies, provided with at least one assistive tool 2, for users suffering from movement and/or communication disorders.

System 1 comprises an electronic communication interface 10, at least one biometric sensor 11, a calibration module 12 and a processing unit 13.

The electronic communication interface 10 is configured to present the user with a plurality of sensory stimuli, each associated with a command and/or a piece of information that the user may want to select and/or to provide.

The at least one biometric sensor 11 is adapted to be applied to the user to detect at least one biometric activity of the user and to generate a respective biometric electrical signal (SB, SBc, SBr) representative of the biometric activity detected.

The calibration module 12 is configured to record, in an initial system calibration step in which the user's biometric activity is a voluntary biometric activity conventionally considered as indicative of the user's will to respectively select a command and/or a piece of information, one or more signal characteristics CS associated with the biometric electrical signal SBc detected in the presence of said at least one voluntary biometric activity.

The processing unit 13 is configured to recognize, based on a comparison between the biometric electrical signal detected SBr and the one or more signal characteristics CS recorded, the voluntary biometric activity of the user and the related command and/or piece of information that the user wants to select, upon a sensory stimulus perceived.

The processing unit 13 is also configured to provide control signals (SC1, SC2) both to the electronic communication interface 10 and to the assistive tool 2, based on the recognition of the user's will to select.

Such control signals comprise at least one signal for controlling the presentation of sensory stimuli SC1, which is adapted to manage the presentation of sensory stimuli based on the user's will, and further comprise at least one control signal to the assistive tool SC2, based on a command and/or a piece of information, among those presented to the user, selected by the user and recognized by the processing unit 13.

The electronic communication interface 10 is configured to present the sensory stimuli based on the at least one presentation control signal SC1, if present, and to present an automatic and predefined sequence of sensory stimuli, in the absence of the presentation control signal SC1.

It is worth noting that the assistive technologies to which reference is made in the present description comprise for example, "augmentative alternative communication", the control of domotic devices, the control of an electric wheelchair. The assistive tools referred to therefore may be for example, an electric wheelchair for disabled persons, various types of domotic devices, robots, etc.

It is worth noting that each of the aforesaid biometric electrical signals (SB, SBc, SBr) generated by the biometric sensors may be an electric or electronic signal, in analog or digital format, and if it is in the analog format, it may be converted into the digital format prior to the processing, the formats in themselves being well known.

It is also worth noting that each of the aforesaid control signals (SC1, SC2) may be an electrical signal, in analog or digital format, or a command message, within the context of an electronic packet transmission of a type which is per se known.

According to one embodiment (shown e.g., in FIG. 2), the at least one biometric sensor 11 comprises a plurality of cerebral electrical signal sensors 11 adapted to be applied to the user to detect at least one cerebral electrical signal (SB). Moreover, the aforesaid at least one voluntary biometric activity comprises at least one respective movement imagined by the user.

In such a case, the processing unit 13 is configured to recognize, based on a comparison between the cerebral electrical signal detected SBr and the one or more characteristics CS of the cerebral electrical signal recorded SBc during calibration, the movement imagined by the user and the related command and/or piece of information that the user wants to select, upon a sensory stimulus perceived.

According to one implementing option, the cerebral electrical signal sensors 11 comprise electroencephalographic sensors EEG, which are applicable to the user's head.

Therefore, in such a case, the system of the invention provides the recognition, by means of EEG sensors, of cerebral electrical signals correlated for example, with actions of imagined movements (forwards, backwards, up, down, right, left).

According to another embodiment, the at least one biometric sensor 11 comprises at least one user's movement sensor 11 adapted to be applied to one or more parts of the user's body to detect movements thereof; and the aforesaid at least one voluntary biometric activity comprises at least one respective movement made by the part of the user's body to which the at least one biometric sensor 11 is applied.

According to one implementing option, the aforesaid at least one movement sensor 11 comprises an accelerometer, applicable to a finger, for detecting the movement thereof, or several accelerometers, applicable to arms, legs, or other parts of the user's body.

According to other implementing options, the movement sensor 11 comprises one or more electromyographic sensors adapted to recognize muscular contraction movements; or infrared movement sensors for detecting for example, a movement of a user's eyelid.

According to another embodiment, the at least one biometric sensor 11 comprises at least one eye movement sensor adapted to detect and/or track the user's eye movements; and the aforesaid at least one voluntary biometric activity comprises at least one respective eye movement by the user.

According to one implementing option, the eye movement is detected by means of a "gaze tracking" sensor, per se known, capable of detecting pupil movements of the user's eye from an initial base position towards one of the four sides of a screen.

According to other possible embodiments, the biometric sensors 11 may be other biometric sensors made available by the art.

It is worth noting that in the various above-described embodiments, in various application examples, the movements imagined or performed by the user (detected by the biometric sensors) may be considered representative of the user's will to control respective corresponding movements of the assistive tool, or to control respective corresponding movements of the pointer on the electronic display screen (in this latter case, the forwards/backwards movement may be correlated for example, with a will to select/deselect). In other examples, also included in the invention, each of the movements imagined or performed, which can be detected and recognized by the system, may be conventionally associated with a command and/or a piece of information of any type, also different from a physical movement.

Referring now to the aforesaid "sensory stimuli" presented to the user by the electronic communication interface 10, it is worth noting that according to various possible embodiments, such sensory stimuli comprise images and/or symbolic icons 21, 22, 23, 24, 25 visually displayed, and/or sounds and/or tactile stimuli.

In particular, in applications for sighted users, visual stimuli (images or symbolic icons, and more generally a graphical user interface on an electronic display screen) are preferably used as sensory stimuli.

Moreover, in particular implementing options, additional audible or tactile return (or feedback) signals may be provided, also for sighted users, by means of the electronic communication interface, the signals coming from the processing unit or from the assistive tool.

In applications for visually-impaired users, non-visual stimuli (e.g. audible or tactile stimuli) are used as sensory stimuli.

According to one implementation example, the electronic communication interface provides the user with suitable feedback by means of a combination of graphs, sounds and tactile feedback obtained for example, by means of specific mechanical actuators.

In accordance with one embodiment of the system, the electronic communication interface 10 comprises a scanning communication interface 10 configured to present the user with a scan of sensory stimuli (e.g., a sequence of images or symbolic icons) in sequence.

Figure 3A:
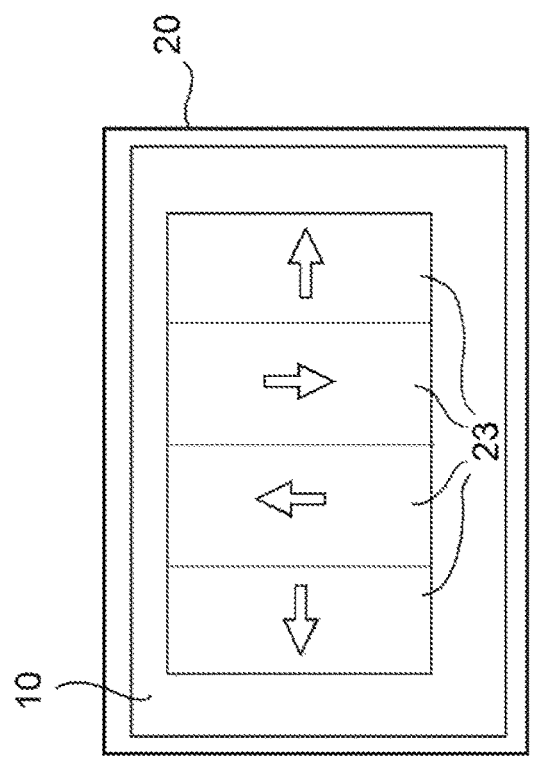
FIGS. 3A-3D represent certain screen examples of an electronic communication interface of the control system, according to respective embodiments.

According to one implementation option (shown e.g., in FIG. 3A), the electronic communication interface 10 comprises an electronic display screen 20 and is configured to present, on such an electronic display screen 20, icons for controlling an electronic window interface (21) capable of bringing up a further icon screen or windows, if selected.

In such a case, the commands and/or pieces of information that can be selected by the user may comprise, for example, a pointer moving command adapted to cause a movement of a pointer 22 on the electronic display screen 20; and also a select/deselect command adapted to select/deselect an icon and/or command and/or box and/or screen area at which pointer 22 is located (or was brought).

In an implementation option, when the electronic communication interface is configured to present an electronic interface 10 with windows and a pointer 22 on an electronic display screen, the voluntary biometric activities may comprise movements which may be imagined or performed by the user, which are bi-uniquely associated with the following commands: movement of the pointer to the right; movement of the pointer to the left; movement of the pointer up; movement of the pointer down; selection/deselection of the icon and/or command and/or screen area on which the pointer is located.

Figure 3B:
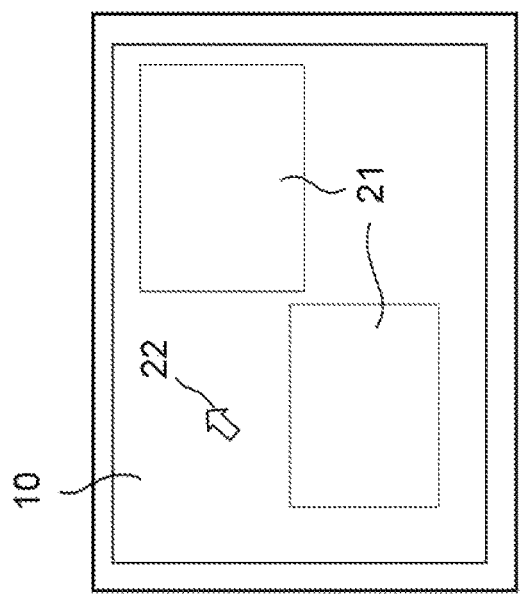

According to another implementing option (shown e.g., in FIG. 3B), the electronic communication interface is configured to present, on an electronic display screen, a sequence of symbolic icons (23) representative of a desired movement direction (for example, the arrows shown on the icons in FIG. 3B may indicate "left", "forwards", "backwards", "right", respectively), and system 1 is capable of interacting with an assistive tool comprising an electric wheelchair 2.

In such a case, the processing unit 13 is configured to control the movements of the electric wheelchair 2 based on the movement symbolic icon (23) selected by the user.

In an implementation alternative, again if system 1 is capable of interacting with an electric wheelchair 2, the electronic communication interface 10 is configured to allow the user to select a desired destination, and the processing unit 13 is configured to control the movements of the electric wheelchair 2 up to the desired destination, based on the destination selection made by the user.

According to a further realization option, the electronic communication interface 10 is configured to show a virtual keypad 24 on an electronic display screen 20, and the processing unit 13 is configured to prepare an electronic message having a text composed by the user by selecting buttons or icons or cells of the virtual keypad.

Figure 3C:
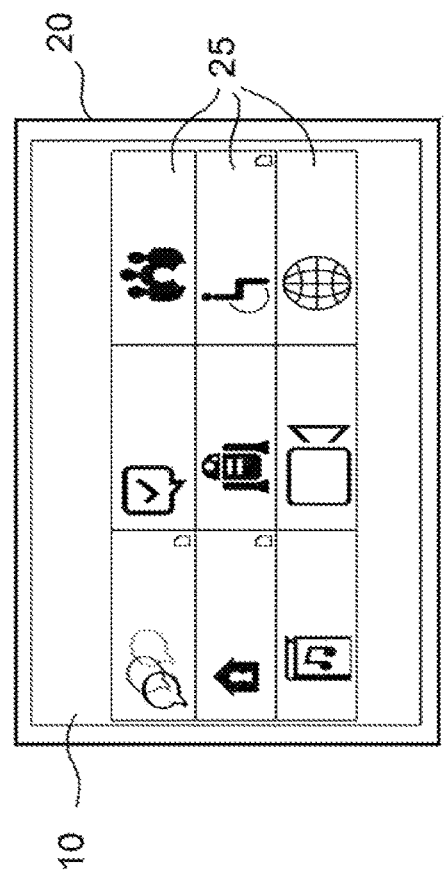

In an implementing option (shown e.g., in FIG. 3C), the aforesaid virtual keypad 24 comprises a sequence of icons (240), each representative of one or a group of alphanumeric characters, the icons being presented in sequence by the electronic communication interface. In the example in FIG. 3C, the various icons or boxes 240 (each containing a group of letters) are highlighted or illuminated in sequence; after the user has selected one them, the user may be shown a series of boxes in sequence, with the various letters of the aforesaid group of letters, so that the user may select the letter desired and gradually compose a text or message in the message window (241).

In another implementing option, the virtual keypad 24 comprises one or more tables comprising rows and columns of cells that can be selected by means of a row-column scan, in which each cell contains an alphanumeric character or a group of alphanumeric characters or a word or a sentence or a reference to a further table of the same type.

In another implementation option, each cell of the table, which consists of at least four cells, contains a group of alphanumeric characters and the processing unit 13 is configured to perform a prediction algorithm adapted to predict the completion of one or more words based only on the groups of characters selected according to the character wanted, and to present the user with the one or more words resulting from the prediction (e.g., in the message window 241), for a possible selection confirmation. For this purpose, various processes—per se known—may be used for predicting the completion of keying-in.

According to a further embodiment, system 1 is capable of interacting with an assistive tool 2 comprising a robot provided with a camera, in which the robot can be controlled by the user.

In such a case, the electronic communication interface 10 is configured to present an image, taken by the camera of the robot, on an electronic display screen and to further show a sequence of command icons of said robot; and the processing unit is configured to control the robot based on the command icon selected by the user.

According to one implementation option, the robot comprises a voice synthesizer that can be controlled by the processing unit 13 so as to act as a remote communicator; the robot is a humanoid robot configured to present an image of the user's face; the electronic communication interface 10 is configured to show a virtual keypad on the electronic display screen for preparing a text for distance communication; and the processing unit 13 is configured to control the voice synthesizer based on the text prepared by the user.

According to another embodiment, system 1 is capable of interacting with an assistive tool comprising one or more domotic devices and/or one or more electronic communication tools.

In such a case, the electronic communication interface 10 is configured to present, on an electronic display screen 20, a sequence of selection and/or control icons 25 (shown e.g., in FIG. 3D) of the one or more domotic devices and/or of the one or more electronic communication tools; and the processing unit 13 is configured to select and/or control the aforesaid one or more domotic devices and/or one or more electronic communication tools based on the selection and/or control icon selected by the user.

Figure 3D:
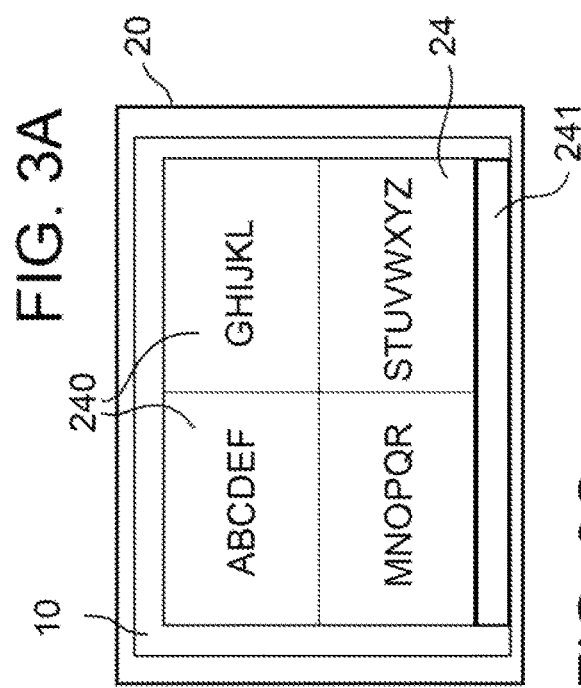

By way of example, the icons in FIG. 3D depict, from left to right, from top to bottom, respectively, command icons of: "communication tools", messaging tools", "social media", "domotic tools", "robots", "wheelchair", "music", "video", "Internet access".

In further implementation examples, the system is also capable of interacting with an assistive tool comprising an augmenting alternative communication software, or an exoskeleton.

Figure 4A:
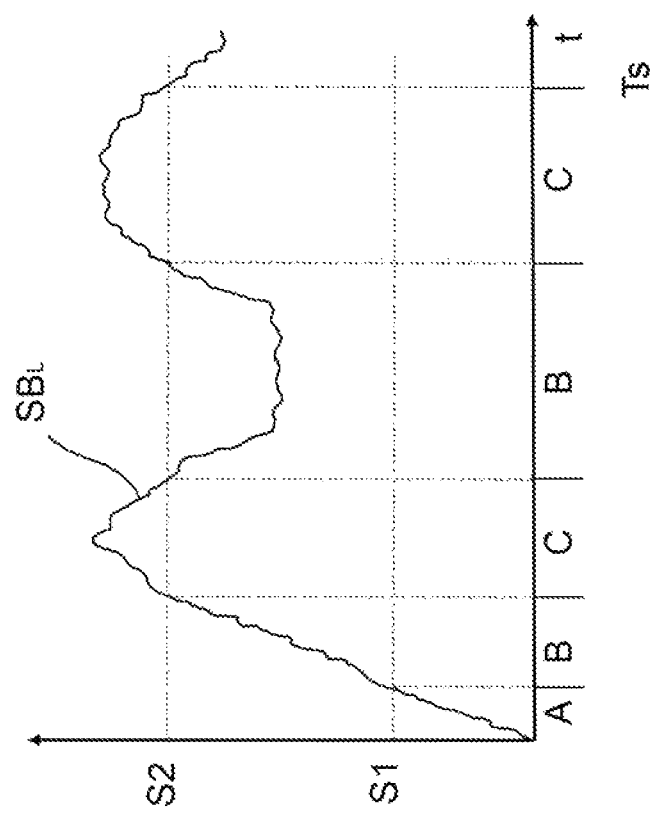
FIGS. 4A-4C show certain diagram examples of signals and certain features of such signals, on which the system of the present invention may operate.
Figure 4B:
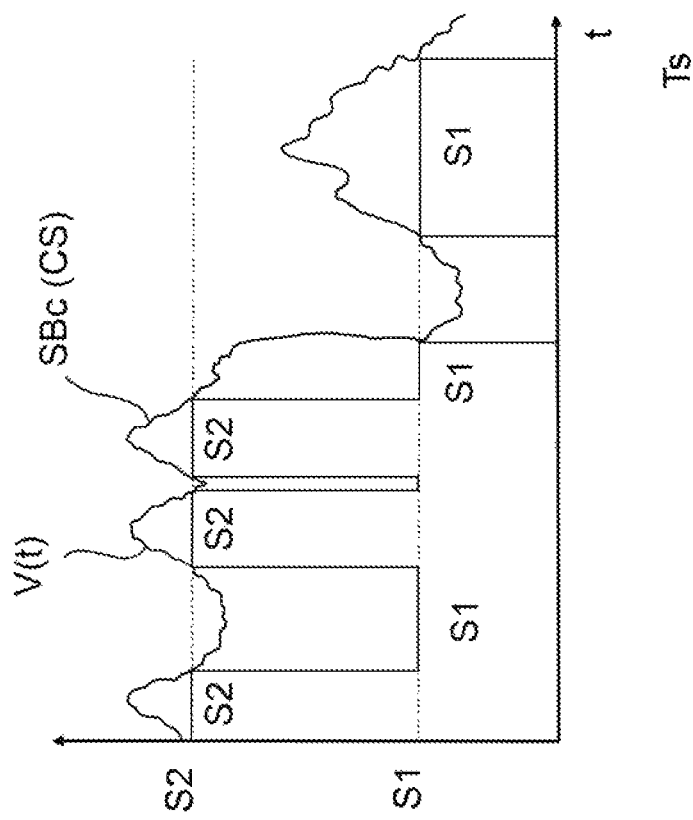
Figure 4C:
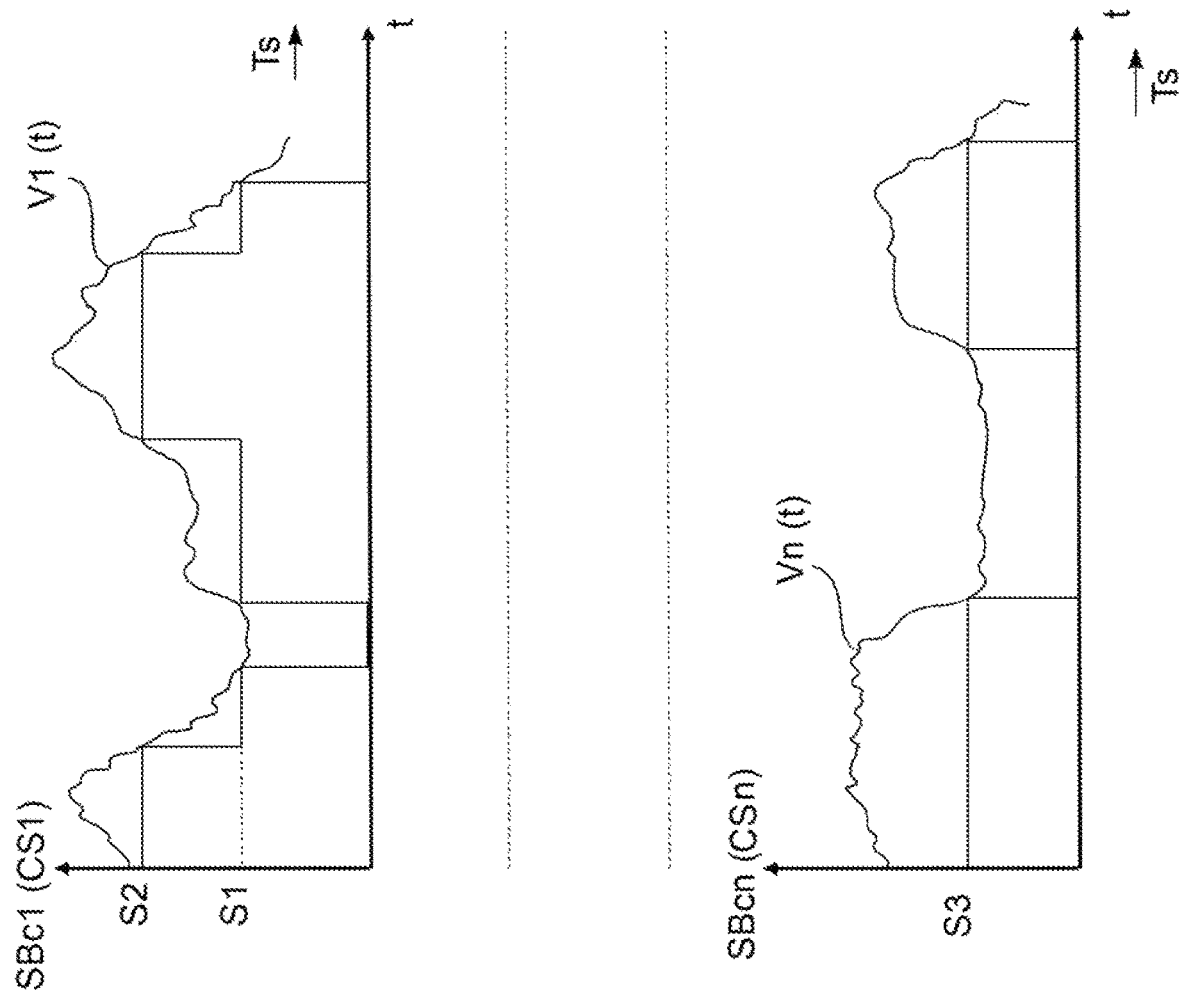

With reference to FIGS. 4A-4C, the biometric electrical signals BS resulting from the detection of other biometric activities are now considered in greater detail, whether they are cerebral electrical signals or are electrical signals of another type, as illustrated above. In this description and in the accompanying drawings, the biometric electrical signals SB detected during calibration are indicated with "SBc", and the biometric electrical signals SB detected during normal use by the user of system 1 are indicated with "SBr".

The detected biometric electrical signals SB are processed by the processing unit 13 to recognize signal characteristics (i.e. signal "patterns") representative of the user's voluntary biometric activities, and therefore of the related commands and/or will associated therewith. The recognition occurs for example, by assessing characteristics of the electric signal(s) detected with respect to corresponding characteristics stored during calibration.

According to one implementing option, the aforesaid one or more signal characteristics comprise a time evolution V(t) of the biometric electrical signal SBc detected during calibration, while the user performs the voluntary biometric activity conventionally defined to enable the selection.

According to one embodiment, the aforesaid one or more signal characteristics comprise one or more thresholds (S1, S2, S3) corresponding to respective one or more threshold values of the biometric electrical signal SBc detected during calibration.

In such a case, system 1 is further configured to define and store the aforesaid one or more biometric electrical signal thresholds (S1, S2, S3) identified during the initial system calibration step; and the processing unit 13 is configured to compare the biometric electrical signal detected SBr with such one or more thresholds (S1, S2, S3) in order to recognize or not to recognize the presence of the user's will to select.

In a particular implementing option (shown for example in the diagram in the lower part of FIG. 4C), a single threshold S3 is stored and the processing unit 13 is configured to recognize the presence of the user's will to select when the biometric electrical signal detected SBr exceeds such a threshold S3 for a predetermined selection time interval Ts.

In other implementing examples comprised in the invention, other features of each biometric electrical signal detected, either in the time domain or in the frequency domain, may be recognized and assessed.

It is worth noting that a plurality of various processing and recognition strategies may be developed based on the teachings indicated above, and therefore they are comprised in the invention. Such strategies are based on various degrees of freedom: the detection of one or more biometric electrical signals; the assessment of one or more signal characteristics for each biometric electrical signal detected, and the comparison with one or more features saved during calibration; the comparison with one or more intensity thresholds so as to cause one or more intensity ranges for each voluntary biometric activity so that each voluntary biometric activity (according to the intensity and the persistence of the signal) may correspond to one or more commands or pieces of information.

FIGS. 4A and 4B depict a biometric electrical signal SBc during calibration and the definition of the thresholds, and a biometric electrical signal SBr detected during the normal use of the system applied to the user and interpreted according to the thresholds defined during calibration, respectively.

Such FIGS. 4A and 4B show an implementation option of system 1, in which multiple thresholds are stored (in the example, two thresholds S1 and S2), which are adapted to define a plurality of signal intervals (in the example depicted, "A", "B", "C"); the processing unit 13 is configured to recognize a multiple choice command by the user, each command ("A", "B", "C") being associated with a respective signal interval ("A", "B", "C") of the aforesaid plurality based on the persistence of the biometric electrical signal detected SBr within the respective signal range for a predetermined selection time interval Ts.

FIG. 4C shows a further implementation option capable of operating on several biometric electrical signals (and respective signal "patterns"). According to such an implementation option, the calibration module 12 is configured to record one or more signal characteristics CS1, CSn associated with each of a plurality of biometric electrical signals SBc1, SBcn, respectively, corresponding to a respective voluntary biometric activity of a plurality of voluntary biometric activities performed by the user, conventionally considered as representative of a plurality of respective commands and/or pieces of information which the user wants to select.

The processing unit 13 is configured to recognize the voluntary biometric activity, among the plurality of voluntary biometric activities that can be performed by the user, based on a comparison between the biometric electrical signal detected SBr and the one or more signal characteristics recorded CS1, CSn.

The processing unit 13 is further configured to recognize the user's related will to select the respective command and/or piece of information from among said plurality of commands and/or pieces of information.

According to one implementing example referring to the command of a scanning electronic communication interface, the scanning interface 10 is configured to: slow down the scanning velocity upon an increasing trend of the biometric electrical signal detected SBr, while it is still below the threshold; stop the scan when the threshold is exceeded by the biometric electrical signal detected SBr; confirm the selection of the piece of information at which the scan stopped if the biometric electrical signal detected SBr remains above the threshold for a time equal to or greater than said selection time interval Ts.

According to another implementing example, the processing unit 13 is further configured to provide to the user, upon a detected biometric electrical signal perceived, but lower than a threshold, a graphical feedback given by the slowing down of the scanning advancement and/or an audio feedback by means of a preset sound and/or a tactile feedback provided by a movement of a mechanical actuator on the surface of the user's skin; or, upon a biometric electrical signal detected above a threshold, a graphical feedback given by a stop of the scanning interface advancement on the selected element and an activation of a "progress bar" at the same element and/or an audio feedback provided by a sound with specific tone and/or a tactile feedback provided by the continuation of the actuator movement on the surface of the user's skin.

In one realization option, the aforesaid one or more thresholds S1, S2, S3 and the selection time interval Ts can be set in a personalized manner.

According to various embodiments of system 1, the processing unit 13 is configured to carry out the recognition of the signal pattern representative of the user's will based on one or more of the following parameters: scanning velocity at which the scanning interface operates (when a scanning interface is involved); value of each of the one or more thresholds; selection time interval Ts (defined as the time required to the user to maintain the action beyond a given selection threshold, in order to avoid false positives due to repetitive involuntary actions); false de-selection time interval defined so as to filter and ignore possible transitions between thresholds that are of brief duration and involuntary; relaxation time interval during which the user should not perform or imagine actions, before the system begins to analyze the biometric signal (used for example when starting a scan and after a selection, in order to avoid false positives).

By virtue of the features illustrated above, which are considered in a consistent way both during the calibration step by the calibration module 12 and during the recognition step by the processing unit 13, certain parameters can be personalized so as to adapt the operating patterns of the system to the user's psycho-physical features and to the type of sensors. In fact, all the parameters mentioned above can be set so they can be controlled by the system operator, and they are calibrated in a personalized manner.

According to one embodiment, system 1 comprises at least one microprocessor device 15 configured to perform the functions of the aforesaid calibration module 12 and processing unit 13, and to control the electronic communication interface 10.

The microprocessor device 15 (shown in FIG. 2) may operate, for example, based on a suitable software recognition module, therein saved, capable of recognizing specific representative patterns consisting, for example, of sequences of simple actions or combinations of actions, and capable of associating the patterns with specific commands (CS1, CS2) for the electronic communication interface 10 and/or for the assistive tool 2. The patterns are defined in order to significantly reduce the number of errors associated with the interpretation of the cerebral electrical signals.

Moreover, to perform the calibration functions, the microprocessor device 15 may operate, for example, based on a suitable calibration software module, therein saved, capable of calibrating patterns according to the user's psycho-physical features and the type of sensor.

According to an implementation option, the acquired biometric electrical signals (e.g., the cerebral signals) concerning a single action of the user are quantized by setting suitable threshold values.

As already noted above, it is possible to use simply a single threshold, by means of which a sort of switch with ON/OFF behavior may be implemented. In other more complex implementing examples, a plurality of thresholds may be set adapted to define a plurality of ranges, each of which being associated with a different command or control action.

Below, to provide an even more detailed illustration of the features of the invention, certain specific examples are provided, given by way of non-limiting example and relating to the case in which the biometric signal is a cerebral electrical signal.

In one example, the electronic communication interface 10 is controlled by means of the single action of imagined movement of forwards push, using three threshold levels. Here, system 1 proposes the selection of a different element of the electronic communication interface 10 as the signal varies. For example, "Communicator" element when the first threshold is exceeded, "Domotic" element when the second threshold is exceeded, "Wheelchair control" element when the third threshold is exceeded. The selection is confirmed by maintaining the signal corresponding to the action at the desired threshold for a given interval of time (i.e., the "selection time" Ts defined previously).

In another example, the electronic communication interface 10 is controlled by means of a single action with the use of a single threshold: the system is configured so as to consider the signal related to the single action of imagined movement of forwards push, with a single threshold equal e.g. to 30% of the end scale value of the signal. The interface here is a of scan type, i.e., it alternatively proposes the selection of a different element (e.g. "Communicator", "Domotic", "Wheelchair control"). When the user imagines the chosen action and the related cerebral signal remains below the threshold, the scan slows down proportionately as the signal increases; if the cerebral signal exceeds the threshold, the scan stops and the selection is confirmed after a pre-defined time interval (the "selection time" Ts). If the imagined action lasts less than the selection time Ts, the scan resumes.

In a further example, to allow visually impaired and/or deaf users to orient themselves when using the system (think of conditions of apparent coma, ALS with consequences of total paralysis, etc.), the electronic communication interface 10 provides the user with a plurality of feedback signals, i.e., also sounds and tactile feedback, in addition to graphical-type signals. For example, it is considered the case of a scan interface controlled by means of a single action (such as the "forwards push") with the use of a single threshold. Assuming that the interface consists of 9 cells arranged over 3 rows, corresponding to just as many selectable elements, the scan first proceeds in the vertical direction, each time proposing the selection of one of the three rows, then, once the row has been selected, the scan proceeds in horizontal direction, each time proposing the selection of one of the three cells.

From the time the scan is activated, a first feedback will be given upon the selection proposed, that is by highlighting it by means of a specific color, and/or a different sound as the position of the row/column varies, and/or tactile feedback on a different position of the skin (by means of specific mechanical actuators).

Two further groups of feedback signals are generated upon the action of the user's forwards push. A first group of feedback signals, corresponding to a push below the threshold, may comprise a graphical feedback given by the slowing down of the scanning advancement, an audio feedback given by a preset sound, a tactile feedback given by a movement of a mechanical actuator on the surface of the skin. A second group of feedback signals, corresponding to a push above the threshold, may comprise a graphical feedback given by the stopping of the scanning advancement on the chosen element and of the activation of a progress bar at the chosen element, an audio feedback given by a sound with a different tone from the first, a tactile feedback given by the continuation of the movement of the actuator on the surface of the skin.

A method for controlling assistive technologies, provided with at least one assistive tool, for users suffering from movement and/or communication disorders, is herein below described.

Firstly, the method provides the step of recording, by means of a calibration module 12, in an initial calibration step, of one or more signal characteristics CS associated with the biometric electrical signal SBc detected in the presence of at least one respective voluntary biometric activity of the user, which is conventionally considered as indicative of the user's will to select a command and/or a piece of information.

Then, the method provides presenting the user, by means of an electronic communication interface 10, with a plurality of sensory stimuli, each associated with a command and/or a piece of information which the user may want to select and/or provide; then, detecting at least one biometric activity of the user, by means of at least one biometric sensor 11, during the presentation of the sensory stimuli, and generating a respective biometric electrical signal SBc representative of the biometric activity detected; then, comparing, by means of a processing unit 13, the biometric electrical signal detected SBr and the one or more signal characteristics CS recorded in the calibration module; and recognizing, by means of the processing unit 13, the biometric activity performed by the user and the user's related will to select, based on such a comparison.

Finally, the method comprises providing, by means of the processing unit 13, control signals SC1, SC2 both to the electronic communication interface 10 and to the assistive tool 2, based on the recognition of the user's will to select.

The aforesaid control signals SC1, SC2 comprise at least one sensory stimuli presentation control signal SC1 adapted to manage such a presentation based on the user's will; and at least one control signal to the assistive tool SC2, based on a command and/or a piece of information, among those presented to the user, selected by the user and recognized by the processing unit 13.

The aforesaid presentation step comprises presenting the sensory stimuli based on the at least one presentation control signal SC1, if present, and presenting an automatic and predefined sequence of sensory stimuli, in the absence of the presentation control signal SC1.

According to a particular embodiment of the method, the aforesaid step of recording comprises recording one or more signal characteristics CS associated with a cerebral electrical signal corresponding to a respective movement imagined by the user, which is conventionally considered as indicative of the user's will to select a command and/or a piece of information.

The aforesaid step of detecting comprises detecting a cerebral electrical signal SBr of the user, by means of a plurality of cerebral electrical signal sensors 11, during the presentation of the sensory stimuli.

The aforesaid step of comparing comprises comparing, by means of the processing unit 13, the cerebral electrical signal detected SBr and the one or more signal characteristics (CS) recorded in the calibration module (12).

The aforesaid step of recognizing comprises recognizing, by means of the processing unit 13, the movement imagined by the user and the user's related will to select, based on the comparison.

According to one implementation option of the method, the presentation step comprises presenting the user with a scan of sensory stimuli in sequence.

According to various implementing options of the method, it is performed by means of a system 1 according to any one of the system embodiments described above.

As can be noted, the object of the present invention is fully achieved by the system, in the light of the functional and structural features thereof.

In fact, the above-described system allows an ample plurality of patients to provide commands and/or pieces of information to express their will in a simple manner and based on biometric activities that the patient is able to perform.

The interaction with the system is facilitated by the features of the communication interface. In particular, the system is advantageously user-friendly also because it allows the user/patient to control both the electrical communication interface and the assistive tool.

Moreover, the various embodiments of the system allow the use of the system itself by users/patients suffering from a wide set of disabilities or illnesses, thus extending the field of application; each patient may select the embodiment most suited to his/her conditions.

The reliability of the interpretation of the patient's commands, and therefore the correspondence with the patient's will, is improved due to the processing features of the above-described signals provided in the system.

Finally, the system provides a significant versatility of use, since it may be used in combination with a wide variety of assistive tools.

Similar advantages can be identified with reference to the method carried out by means of the above system.

Those skilled in the art may make several changes and adaptations to the above-described embodiments of the system and method, and may replace elements with others which are functionally equivalent in order to meet contingent needs, without departing from the scope of the following claims. All the features described above as belonging to a possible embodiment may be implemented regardless of the other embodiments described.

The invention claimed is:

1. A system for controlling assistive technologies, provided with at least one assistive tool, for users suffering from movement and/or communication disorders, the system comprising:

an electronic communication interface, configured to present a user with a plurality of sensory stimuli, each of the stimuli associated with a command and/or a piece of information that the user may want to select and/or to provide;

at least one biometric sensor, suitable to be applied to the user to detect at least one biometric activity of the user and to generate a respective biometric electrical signal representative of the biometric activity detected;

a calibration module, configured to record, in an initial system calibration step, wherein the user's biometric activity is a voluntary biometric activity conventionally considered as indicative of the user's will to respectively select a command and/or a piece of information, one or more signal characteristics, associated with the biometric electrical signal detected in presence of said at least one voluntary biometric activity, wherein said at least one voluntary biometric activity comprises at least one respective movement imagined by the user;

a processing unit, configured to recognize, based on a comparison between the biometric electrical signal detected and the one or more signal characteristics recorded, the voluntary biometric activity of the user and the related command and/or piece of information the user wants to select, upon a sensory stimulus perceived;

the processing unit being configured to provide control signals to the electronic communication interface and to the assistive tool, based on recognition of the user's will to select, wherein the control signals comprise:

at least one signal for controlling presentation of sensory stimuli, suitable to manage said presentation based on the user's will;

at least one command signal to the assistive tool, based on a command and/or a piece of information, among the command and/or a piece of information presented to the user, selected by the user and recognized by the processing unit;

the electronic communication interface being configured to present the sensory stimuli based on the at least one presentation control signal, if present, and to present an automatic and predefined sequence of sensory stimuli, in absence of the presentation control signal;

wherein said one or more signal characteristics comprise one or more thresholds, corresponding to respective one or more threshold values of the biometric electrical signal detected during calibration;

wherein the system is configured to define and store said one or more biometric electrical signal thresholds identified during the initial system calibration step;

wherein the processing unit is configured to compare the biometric electrical signal detected with said one or more thresholds, in order to recognize or not recognize presence of the user's will to select; and wherein the processing unit is further configured to provide the user with:

upon a detected electrical biometric signal perceived, yet lower than a threshold, a graphical feedback given by slowing down of scanning advancement, and/or an audio feedback by a preset sound, and/or a tactile feedback provided by a movement of a mechanical actuator on a surface of the user's skin; or upon an electrical biometric signal detected above a threshold, a graphical feedback given by a stop of the scanning interface advancement on a selected element and an activation of a progress bar at the selected element, and/or an audio feedback provided by a sound with specific tone, and/or a tactile feedback provided by continuation of the mechanical actuator movement on the surface of the user's skin.

2. The system according to claim 1, wherein:
said at least one biometric sensor comprises a plurality of cerebral electrical signal sensors, adapted to be applied to the user to detect at least one cerebral electrical signal;
the processing unit is configured to recognize, based on a comparison between the cerebral electrical signal detected and the one or more characteristics of the cerebral electrical signal recorded during calibration, movement imagined by the user and a related command and/or piece of information that the user wants to select, upon a sensory stimulus perceived.

3. The system according to claim 1, wherein:
said at least one biometric sensor comprises at least one user's movement sensor, adapted to be applied to one or more parts of the user's body to detect movements thereof;
said at least one voluntary biometric activity comprises at least one respective movement made by a part of the user's body to which the at least one biometric sensor is applied.

4. The system according to claim 1, wherein:
the at least one biometric sensor comprises at least one eye movement sensor, adapted to detect and/or track user's eye movements;
said at least one voluntary biometric activity comprises at least one respective eye movement by the user.

5. The system according to claim 1, wherein said sensory stimuli comprise: images and/or symbolic icons visually displayed; and/or sounds and/or tactile stimuli;
and wherein the electronic communication interface comprises a scanning communication interface, configured to present the user with a scan of successive sensory stimuli.

6. The system according to claim 1, wherein the electronic communication interface comprises an electronic display screen and is configured to present on said electronic display screen command icons of an electronic window interface, capable of bringing up, if selected, a further icon screen, and wherein the commands and/or information selectable by the user comprise:
a pointer moving command, adapted to cause a movement of a pointer on the electronic display screen;
a select/deselect command, adapted to select/deselect an icon and/or command and/or box and/or screen area at which the pointer is located.

7. The system according to claim 1, wherein the electronic communication interface is configured to show on an electronic display screen a sequence of symbol icons representative of a desired movement direction, and/or to allow the user to select a desired destination, and wherein:
the system is capable of interacting with the assistive tool comprising an electric wheelchair;
the processing unit is configured to control movements of the electric wheelchair based on the movement symbol icon selected by the user, and/or to control the movements of the electric wheelchair up to a desired destination, based on a destination selection made by the user.

8. The system according to claim 1, wherein the electronic communication interface is configured to show a virtual keypad on an electronic display screen, and wherein the processing unit is configured to prepare an electronic message having a text composed by the user by selecting buttons or icons or cells of said virtual keypad.

9. The system according to claim 8, wherein said virtual keypad comprises:
either a sequence of icons, each representative of one or a group of alphanumeric characters, presented in sequence by the electronic communication interface; or
one or more tables, comprising rows and columns of cells that can be selected by a row-column scan, wherein each cell contains an alphanumeric character, or a group of alphanumeric characters, or a word, or a sentence, or a reference to a further table of a same type, wherein each cell of the table contains a group of alphanumeric characters, and the processing unit is configured to perform a prediction algorithm, adapted to predict completion of one or more words based on first characters selected, and to present the user with the one or more words derived from the prediction, for a possible selection confirmation.

10. The system according to claim 1, wherein:
the system is capable of interacting with the assistive tool comprising a robot provided with a camera, wherein the robot can be controlled by the user;
the electronic communication interface is configured to present an image taken by the camera of the robot on an electronic display screen and to present a sequence of command icons of said robot;
the processing unit is configured to control the robot based on the command icon selected by the user;
the robot comprises a voice synthesizer that can be controlled by the processing unit to act as a remote communicator;
the robot is a humanoid robot configured to present an image of the user's face;
the electronic communication interface is configured to show a virtual keypad on the electronic display screen for preparing a text for distance communication;
the processing unit is configured to control the voice synthesizer based on the text prepared by the user.

11. The system according to claim 1, capable of interacting with the assistive tool comprising one or more domotic devices and/or one or more electronic communication tools, wherein:
the electronic communication interface is configured to present on an electronic display screen a sequence of selection and/or control icons of the one or more domotic devices and/or of the one or more electronic communication tools;
the processing unit is configured to select and/or control said one or more domotic devices and/or one or more electronic communication tools, based on the selection and/or control icon selected by the user.

12. The system according to claim 1, wherein a single threshold is stored, and wherein the processing unit is configured to recognize the presence of the user's will to select when the biometric electrical signal detected exceeds said threshold for a predetermined selection time interval, wherein said threshold and said selection time interval can be set in a personalized manner.

13. The system according to claim 1, wherein multiple thresholds are stored, suitable to define a plurality of signal intervals;
and wherein the processing unit is configured to recognize a multiple choice command, activated by the user, each command being associated with a respective signal interval of said plurality, based on persistence of the electrical biometric signal detected within the respective signal range, for the selection time interval, wherein said multiple thresholds and said selection time interval can be set in a personalized manner.

14. The system according to claim 1, wherein the processing unit is configured to carry out the recognition of the user's will based on one or more of the following parameters:
   scanning velocity at which the scanning interface operates;
   value of each of the one or more thresholds;
   selection time interval;
   false de-selection time interval, defined to filter and ignore possible transitions between thresholds that are of brief duration and involuntary;
   relaxation time interval, during which the user must not perform or imagine actions, before the system begins to analyze the biometric signal.

15. The system according to claim 1, wherein:
   the calibration module is configured to record one or more signal characteristics associated with each of a plurality of electrical biometric signals, corresponding to a respective voluntary biometric activity of a plurality of voluntary biometric activities performed by the user, conventionally considered as representative of a plurality of respective commands and/or information which the user wants to select;
   the processing unit is configured to recognize the voluntary biometric activity, among said plurality of voluntary biometric activities that can be performed by the user, based on a comparison between the electrical biometric signal detected and the one or more signal characteristics recorded; and
   the processing unit is further configured to recognize a relative will to select, by the user, the respective command and/or piece of information, from among said plurality of commands and/or pieces of information.

16. Method for controlling assistive technologies, provided with at least one assistive tool, for users suffering from movement and/or communication disorders, the method comprising:
   recording, by a calibration module, in an initial calibration step, one or more signal characteristics associated with a biometric electrical signal detected in a presence of at least one respective voluntary biometric activity of a user, which is conventionally considered as indicative of the user's will to select a command and/or a piece of information, wherein said one or more signal characteristics comprise one or more thresholds, corresponding to respective one or more threshold values of the biometric electrical signal detected during the initial calibration step;
   defining and storing said one or more biometric electrical signal thresholds identified during the initial system calibration step;
   presenting the user, by an electronic communication interface, with a plurality of sensory stimuli, each of the stimuli associated with a command and/or a piece of information which the user may want to select and/or provide;
   detecting at least one biometric activity of the user, by at least one biometric sensor, during presentation of the sensory stimuli, and generating a respective biometric electrical signal representative of the biometric activity detected, wherein said at least one voluntary biometric activity comprises at least one respective movement imagined by the user;
   comparing, by a processing unit, the biometric electrical signal detected and said one or more signal characteristics recorded in the calibration module;
   recognizing, by the processing unit, the biometric activity performed by the user and the related will to select, by the user, based on said comparison;
   providing, by the processing unit, control signals to the electronic communication interface and to the assistive tool, based on recognition of the user's will to select;
   upon a detected electrical biometric signal perceived, yet lower than a threshold, the processing unit providing the user with a graphical feedback given by slowing down of scanning advancement, and/or an audio feedback by a preset sound, and/or a tactile feedback provided by a movement of a mechanical actuator on a surface of the user's skin; or
   upon an electrical biometric signal detected above a threshold, the processing unit providing the user with a graphical feedback given by a stop of the scanning interface advancement on a selected element and an activation of a progress bar at the selected element, and/or an audio feedback provided by a sound with specific tone, and/or a tactile feedback provided by continuation of the movement of the mechanical actuator on the surface of the user's skin
   comparing, by the processing unit, the biometric electrical signal detected with said one or more thresholds, in order to recognize or not recognize presence of the user's will to select;
   wherein said control signals comprise:
   at least one sensory stimuli presentation control signal, adapted to manage said presentation based on the user's will;
   at least one command signal to the assistive tool, based on a command and/or a piece of information, among those presented to the user, selected by the user and recognized by the processing unit;
   wherein said presentation step comprises presenting the sensory stimuli based on the at least one presentation control signal, if present, and presenting an automatic and predefined sequence of sensory stimuli, in an absence of the presentation control signal.

17. The method according to claim 16, wherein:
   said recording step comprises recording one or more signal characteristics, associated with a cerebral electrical signal corresponding to the respective movement imagined by the user, which is considered as indicative of the user's will to select a command and/or a piece of information;
   said detecting step comprises detecting a cerebral electrical signal of the user, by a plurality of cerebral electrical signal sensors, during the presentation of the sensory stimuli;
   said comparing step comprises comparing, by the processing unit, the cerebral electrical signal detected and the one or more signal characteristics, recorded in the calibration module;
   said recognizing step comprises recognizing, by the processing unit, the movement imagined by the user and the relative will to select, by the user, based on said comparison.

* * * * *